(12) United States Patent
Hubscher

(10) Patent No.: US 7,629,127 B2
(45) Date of Patent: Dec. 8, 2009

(54) METHOD FOR THE VISUAL DETECTION OF SPECIFIC ANTIBODIES BY THE USE OF LATERAL FLOW ASSAYS

(75) Inventor: Thomas T. Hubscher, Gaithersburg, MD (US)

(73) Assignee: Dexall Biomedical Labs, Inc., Gaithersburg, MD (US)

(*) Notice: Subject to any disclaimer, the term of this patent is extended or adjusted under 35 U.S.C. 154(b) by 73 days.

(21) Appl. No.: 11/038,076

(22) Filed: Jan. 21, 2005

(65) Prior Publication Data

US 2006/0166374 A1 Jul. 27, 2006

(51) Int. Cl.
G01N 33/53 (2006.01)

(52) U.S. Cl. ............... 435/7.1; 435/4; 435/5; 435/287.1; 435/287.7; 435/970; 435/975; 435/7.91; 436/514; 436/518; 436/507; 436/530; 436/807; 436/821; 436/810; 422/56; 422/57; 422/58; 422/60; 422/61

(58) Field of Classification Search ............ 435/4, 435/5, 187.1, 287.7, 970, 975; 436/514, 436/518, 507, 530, 807, 821, 810; 422/56, 422/57, 58
See application file for complete search history.

(56) References Cited

U.S. PATENT DOCUMENTS

| | | | |
|---|---|---|---|
| 4,857,453 A * | 8/1989 | Ullman et al. ............ 435/7.92 |
| 5,200,344 A | 4/1993 | Blaser et al. |
| 5,420,014 A | 5/1995 | Cripps |
| 5,459,041 A | 10/1995 | Blaser et al. |
| 5,547,833 A | 8/1996 | Dorval et al. |
| 5,559,041 A * | 9/1996 | Kang et al. ............... 436/518 |
| 5,567,594 A | 10/1996 | Calenoff |
| 5,622,871 A | 4/1997 | May et al. |
| 5,846,751 A | 12/1998 | Pronovost et al. |
| 5,945,294 A | 8/1999 | Frank et al. |
| 6,060,326 A | 5/2000 | Frank et al. |
| 6,068,985 A | 5/2000 | Cripps |
| 6,485,982 B1 | 11/2002 | Charlton |
| 6,528,325 B1 | 3/2003 | Hubscher et al. |
| 2002/0045195 A1 * | 4/2002 | Hubscher et al. ............ 435/7.9 |

* cited by examiner

Primary Examiner—Bao-Thuy L Nguyen
(74) Attorney, Agent, or Firm—Jonathan E. Grant; Grant Patent Services

(57) ABSTRACT

This disclosure teaches a method and composition for detecting the presence of class specific antibodies reactive with analytes such as bacteria, allergens, autoimmune antigens, viral proteins, haptens, and carbohydrates by lateral flow techniques. In one embodiment of the disclosure, a test sample is added to the test strip, which then migrates to the site of the immobilized allergens, thereby forming a first antibody IgE-allergen complex. A chase release buffer is added upstream to or from the site of the labeled anti-IgE antibodies, which is itself upstream from the sample site. The anti-IgE antibodies migrate downstream to the site of immobilized first complex, thereby forming a second complex indicating the presence of class specific IgE antibodies in the test specimen. In another embodiment of the disclosure, a liquid form of the labeled anti-IgE antibodies can be added to the test strip after the first complex has been formed.

7 Claims, 3 Drawing Sheets

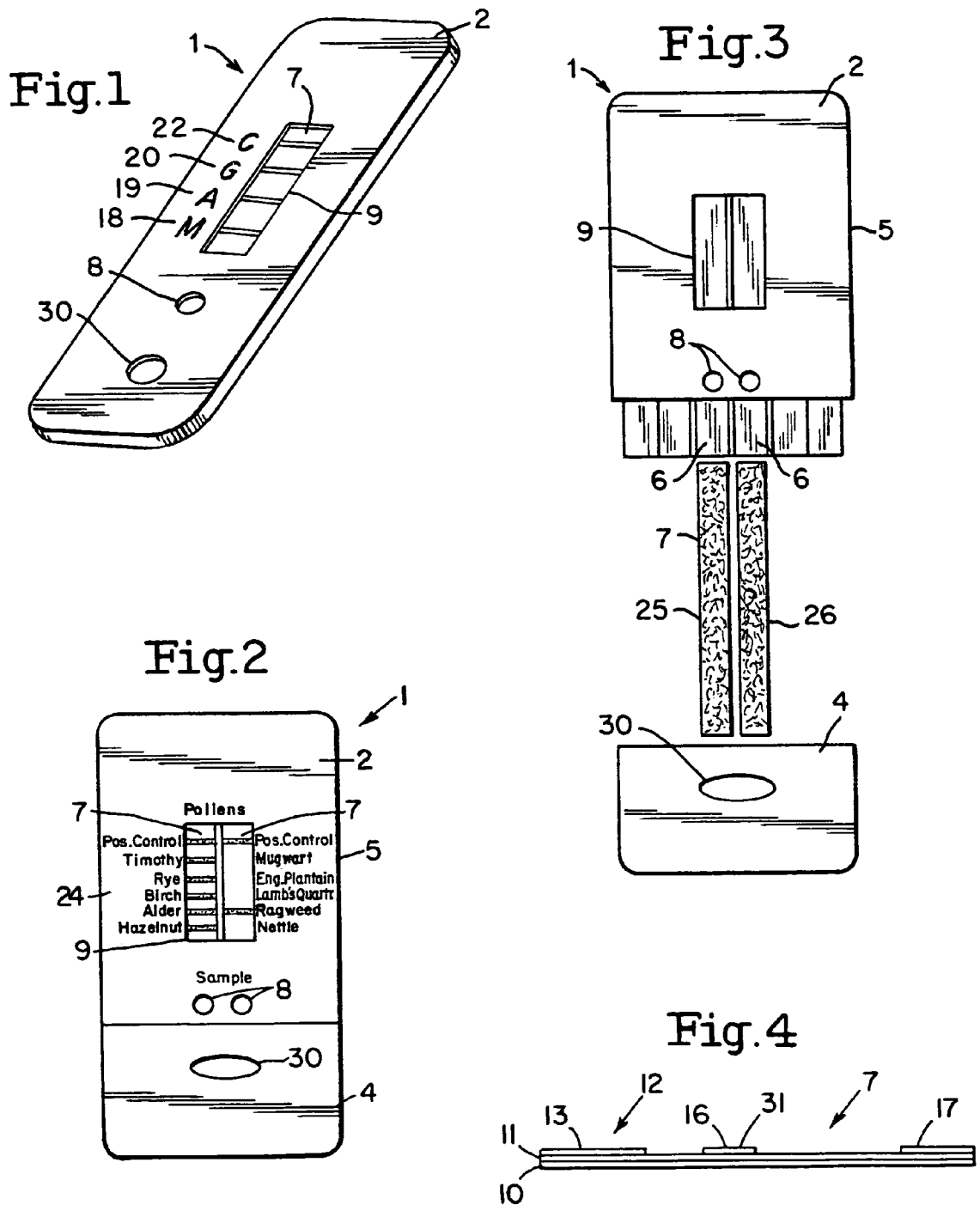

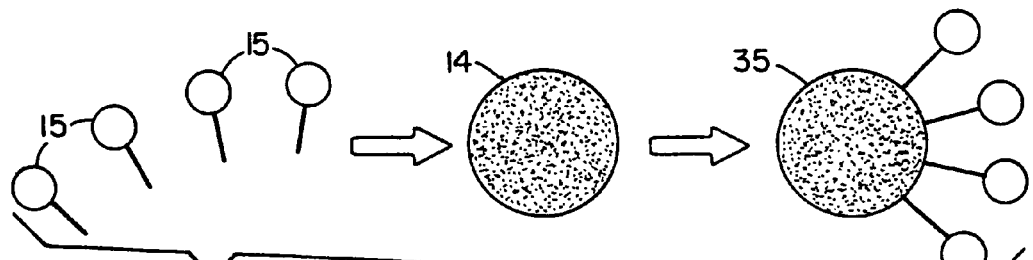
Fig.5
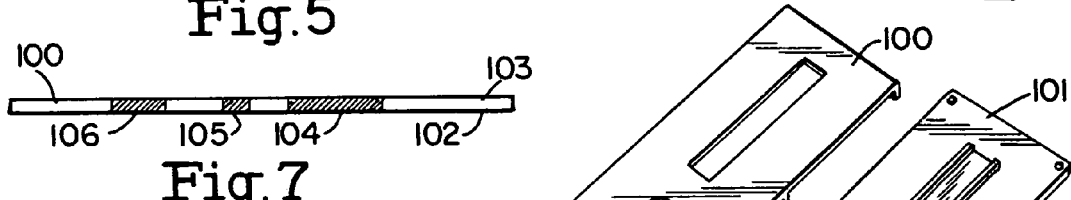
Fig.7  Fig.6
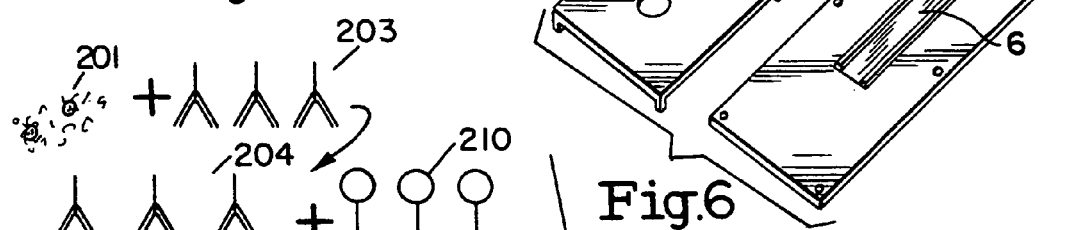
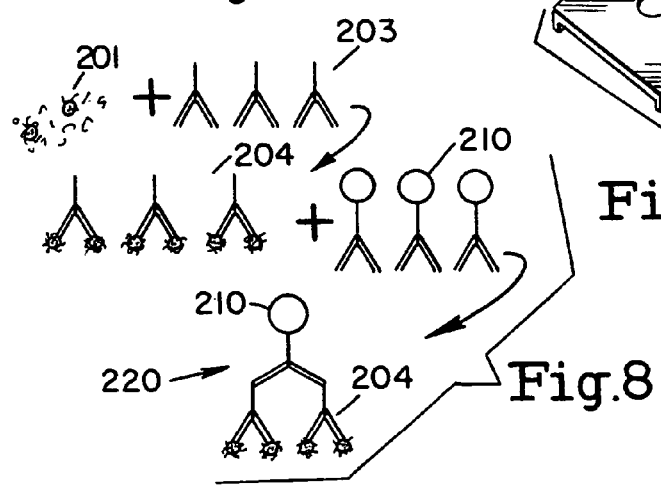
Fig.8
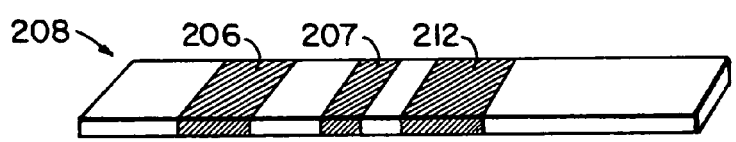
Fig.9
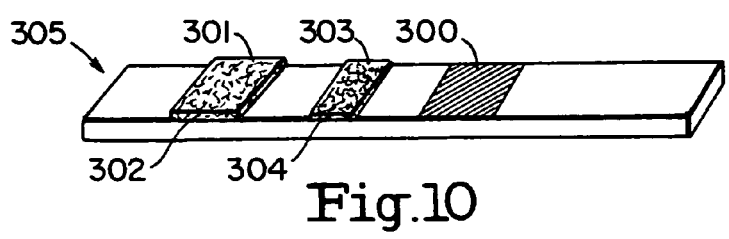
Fig.10

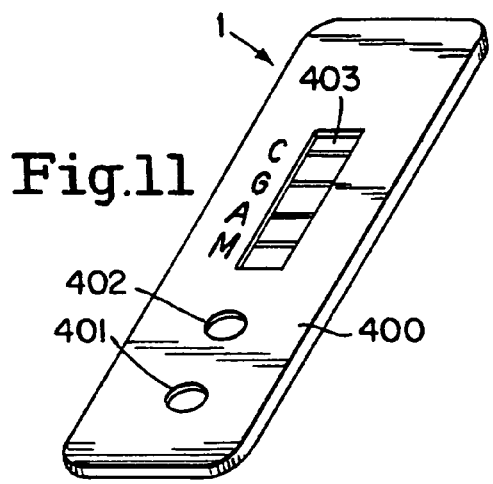
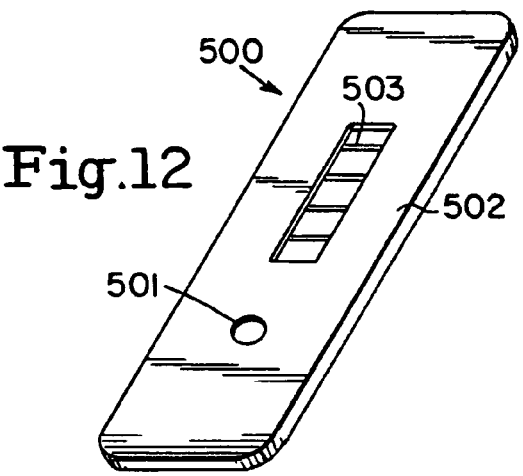
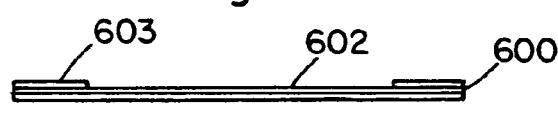
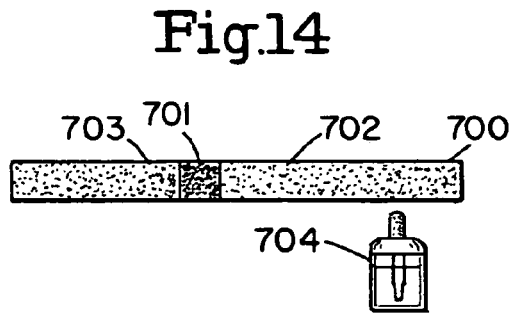
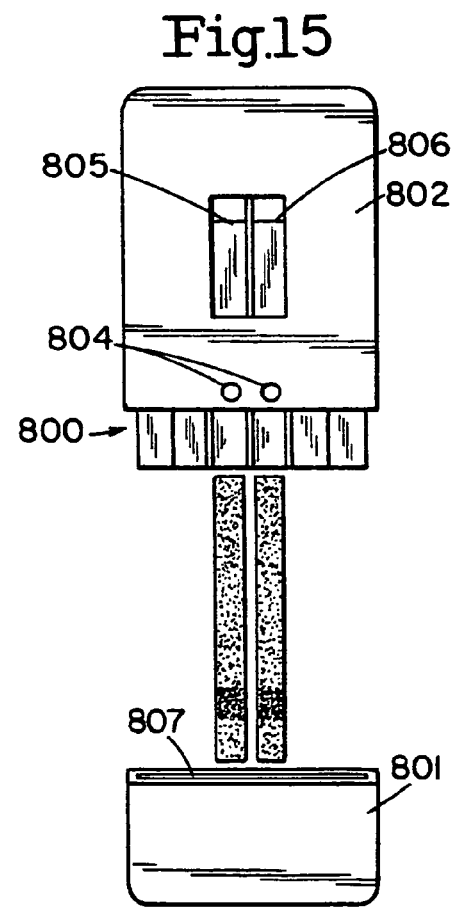

METHOD FOR THE VISUAL DETECTION OF SPECIFIC ANTIBODIES BY THE USE OF LATERAL FLOW ASSAYS

BACKGROUND OF THE DISCLOSURE

1. Field of the Disclosure

The present disclosure discloses a method and composition for detecting the presence of antibodies in human or animal bodily fluids (blood, serum, plasma, urine, colostrum, milk, tears, or saliva) to analytes such as bacteria, Chlamydiae, Rickettsiae, protozoa, allergens, autoimmune antigens, viral proteins, and carbohydrates by lateral flow techniques.

2. Description of the Prior Art

Over the years, numerous patents have been issued involving immuno-chromatographic devices. The standard features of these devices comprise the following:

a) A plastic or paper housing allowing the viewing of a reaction area on a bibulous (lateral flow) strip;

b) an opening at one end of the housing allowing for the addition of sample (urine, blood, plasma, serum or bacteria in a media base);

c) Bibulous material (the lateral flow strip) having immobilized specific binding members (analytes) capable of reacting with antigens or antibodies.

d) A pad of absorbent bibulous material (the absorbent pad) enclosed at the end opposite the sample well and used to absorb transversely flowing sample, buffers and colloids;

e) A strip of bibulous material used in the sample well end to initially absorb the sample being applied;

f) A strip of bibulous material in contact with the sample well material and the lateral flow strip and containing a dried colored solid phase reagent, the solid phase coated with proteins or haptens.

Two types of chromatographic immunoassays are commonly described. In the one, proteins, haptens, or small molecule analytes contained in bodily fluids (urine, blood, plasma, serum, and saliva) are detected. The analytes include hCG, FSH, LH, CKMB, TSH, troponins, myoglobulin, cancer proteins, viralbacterial proteins, haptens, therapeutic drugs, and drugs of abuse.

In the other chromatographic immunoassay, the analyte being detected is (are) human antibody (antibodies) of various classes specifically reactive with agents such as viral or bacterial proteins (HIV, Hepatitis A and C, *H. pylori*, EBV, Rubella, CMV, HSV, Dengue fever, Lyme, Chagas, TB, Toxoplasma, autoimmune antigens, etc.) or allergens (pollens, molds, dust/mites, foods, animal epithelia, etc.). The various analytes are abbreviated VB for simplified use below. When it comes to detecting antibody, three formats are typically used:

1) The colored solid phase [SP] is coated with proteins or lectins [protein A, protein G, lentil lectin, jacalin, concanavilin A, mannan binding protein, wheat germ lectin, peanut lectin and avidchrom] that react with human IgG antibodies. The solid phase may be coated with anti-immunoglobulins that specifically react with IgG, IgM, IgA, or IgE contained in the sample to be analyzed. The bibulous strip would in this case contain the analyte of interest to which the specific antibody contained in the sample reacts.

2) The colored solid phase contains the analyte to which the human immunoglobulins react. The bibulous strip would in this case also contain the analyte of interest to which the specific antibody contained in the sample reacts.

3) The colored solid phase contains the analyte to which immunoglobulins react. The bibulous strip contains proteins directed against various classes of immunoglobulins or substances such as protein A, protein G, lectins, lentil lectin, jacalin, concanavilin A, mannan binding protein, wheat germ lectin, peanut lectin and avidchrom or a mix of antibody to immunoglobulin classes IgG, IgA, IgM and IgE.

U.S. Pat. No. 5,459,041 (Blaser et al.) discloses antigenic compositions for use in diagnostic kits and the like for detecting the presence of antibodies specific for *Campylobacter pylori*, Samples of bodily fluids, for instance, may be contacted with immobilized antigen on a solid phase which is then washed and tested for the occurrence of significant levels of antigen/antibody complex. Levels exceeding a predetermined positive threshold are indicative of antibodies to *Campylobacter pylori* in the sample tested. Kits employing the antigenic compositions of the disclosure preferably include means for detecting the antigen/antibody complex such as materials and reagents for conducting an enzyme-linked immunosorbent assay, Western blot technique, ELISA, liposome-based assay or other known detection tests. The Western blot and ELISA tests used here are for the detection of IgA and IgG antibodies.

U.S. Pat. No. 5,567,594 (Calenoff) discloses a library of isolated and purified antigens specific for a microorganism is a set of individual molecules. The library forms antigen-antibody complexes useful in the context of diagnosing and treating conditions associated with a specific microorganism such as *H. pylori*-induced gastro-duodenal disease. Antigen-antibody complexes with IgA, IgG and IgM are also useful if the antigen is a bacteria. By this multivariate approach, a specific condition is diagnosed with high sensitivity and specificity by determining whether complexes form between a specific antigen library and a biological sample which contains immunoglobulins from an individual. Such libraries also are useful for immunotherapy. Western blot is used to detect IgE antibodies. The method requires enzyme conjugates and enzyme substrates and two wash steps to detect antibodies.

U.S. Pat. No. 5,420,014 (Cripps et al.) discloses a method for detecting a current infection by *H. pylori* in a mammal. The method comprises contacting a mucous secretion [saliva] from said mammal with an immobilized antigen component from *H. pylori* for a time and under conditions sufficient for an IgG antibody in said mucous secretion specific to a antigen component to form a complex therewith and then subjecting said complex to a detecting means which involves an enzyme conjugate and specific substrate.

U.S. Pat. No. 6,068,985 (Cripps) discloses a method which uses saliva to detect IgG in both the Western Blot and ELISA tests. This detection method requires the use of an enzyme conjugate and enzyme substrate and two wash steps to detect the antibody.

U.S. Pat. No. 5,846,751 (Pronovost et al.) discloses a sensitive and specific antigen preparation for the detection of *Helicobacter pylori* in biological samples. The preparation uses a range of antigens derived from size exclusion chromatography of detergent-solubilized *H. pylori* cells and the purified antigen preparation is coated on the solid phase. Serological assays such as ELISA, latex agglutination, and rapid EIA assays are used to detect antibodies to *H. pylori*. The disclosure also uses a lateral flow device to detect total immunoglobulins to *H. pylori*. In this case, the *H. Pylori* antigen is striped on the membrane reaction area and also coated to the colored solid phase. The antibody in the sample reacts first with *H. pylori* gold coated conjugate, and then travels to the membrane reaction area where it reacts with striped *H. pylori*.

U.S. Pat. No. 5,200,344 (Blaser et al) uses a purified p28kd protein from *H. pylori* to detect IgA, IgM and IgG antibody in ELISA and Western Blot. The test requires conjugate and enzyme substrate and two wash steps to detect the antibody.

U.S. Pat. Nos. 6,060,326 and 5,945,294 (Frank et al.) discloses methods to detect canine IgE using a canine Fc epsilon receptor to detect canine IgE antibodies in a biological sample from a canine.

U.S. Pat. No. 5,547,833 (Dorval et al.) discloses a radial flow assay delivery device, and methods of use.

U.S. Pat. No. 5,622,871 (May et al.) discloses an analytical test device useful for example in pregnancy testing, includes a hollow casing constructed of moisture-impervious solid material, such as plastics materials, containing a dry porous carrier which communicates indirectly with the exterior of the casing via a bibulous sample receiving member which protrudes from the casing such that a liquid test sample can be applied to the receiving member and permeate therefrom to the porous carrier, the carrier containing in a first zone a labelled specific binding reagent is freely mobile within the porous carrier when in the moist state, and in a second zone spatially distinct from the first zone unlabelled specific binding reagent for the same analyte which unlabelled reagent is permanently immobilised on the carrier material and is therefore not mobile in the moist state, the two zones being arranged such that liquid sample applied to the porous carrier can permeate via the first zone into the second zone, and the device incorporating an aperture in the casing, enabling the extent (if any) to which the labelled reagent becomes bound in the second zone to be observed. Preferably the device includes a removable cap for the protruding bibulous member. Additionally, May teaches that all of the reagents, analyte reactions, and complexes occur within a single test strip.

U.S. Pat. No. 6,485,982 (Charlton) discloses a test cell and a method for detection of a preselected ligand in a liquid sample such as a body fluid. The test cell includes an elongate outer casing which houses an interior permeable material capable of transporting an aqueous solution and defining a sample inlet, a test volume, and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site which includes a first protein having a binding site specific to a first epitope of the ligand immobilized in fluid communication with the flow path. The test site can be observed through a window of the casing. Like May, this patent teaches that all of the reagents, analyte reactions, and complexes occur within a single test strip.

U.S. Pat. No. 6,528,325 (Hubscher et al.) discloses a method and composition for detecting the presence of class specific antibodies reactive with analytes such as bacteria, allergens, autoimmune antigens, viral proteins, and carbohydrates by lateral flow techniques. In one embodiment of the invention, a test sample obtained from bodily fluids reacts with a gold labeled antigen. The resulting complex travels across the membrane, and along the lateral flow strip. Red colored lines formed in specific locations along the test strip where anti-class specific antibodies have been immobilized indicate the presence of class specific antibodies in the test specimen. In another embodiment of the invention, the lateral flow assay serves as an immunochromatographic screening test for the detection of allergen-specific IgE antibodies in human serum. Test sample reacts with gold labeled anti-IgE antibody. The resulting complex travels across the membrane where immobilized allergens capture the allergen specific IgE-anti-IgE complex. Colored lines are formed in the test areas to indicate the presence of allergen-specific IgE antibodies.

SUMMARY OF THE DISCLOSURE

The proposed disclosure allows for a greatly improved antibody class recognition. In one embodiment of the disclosure, a lateral flow immunoassay device distinguishes at least three classes of antibody. The classes of antibody to be distinguished include IgG, IgA and IgM. A control line reactive with gold particles is also present. The new arrangement on the test strip of the lateral flow assay of the present disclosure greatly improves accuracy and readability.

Specifically, the lateral flow immunoassay device for detecting immune reactants, comprises at least one test strip. Each test strip has a sample site for applying a sample comprising antibodies. There are a plurality of reaction sited downstream from the sample site, with each said reaction site containing a different allergen such that when IgE antibodies come in contact with an antigen to which the IgE antibodies react, a first complex between the sample IgE and the immobilized allergen is formed. In contrast to the prior art colorimetric labeled analyte site comprising a calorimetric labeled anti-IgE antibody, is positioned upstream from said sample site. There is a location on said test strip to add a chase release buffer for the release of the labeled analyte. With the addition of said chase release buffer the labeled analyte (gold labeled anti-IgE), migrates to the site of the at least one first complex, and a colorimetric labeled Anti-IgE antibody-antibody IgE-allergen-complex is formed. This novel arrangement greatly improves the accuracy and readability of positive results In another embodiment of the disclosure, the immunoassay test strip is modified to allow detection of the IgE class of antibody to the many allergens coated sequentially on a bibulous strip.

In another embodiment of the disclosure, IgG reacting protein (which can be protein A, protein G, an antibody to IgG or lectins such as lentil lectin, jacalin, concanavilin A, mannan binding protein, wheat germ lectin, peanut lectin and avidchrom) is added to the sample pad in order to complex the IgG contained in the sample such that the molecular weight of the IgG complex is greater than 1.0 million. This large complex travels sufficiently slower than IgA, IgM, and IgE thereby allowing these antibodies to react prior to the IgG. The various reacted complexes are captured on the bibulous strip coated at three sites with antibody to IgM, IgA and IgG or a protein/lectin reactive with IgG (protein A, protein G, lentil lectin, jacalin, concanavilin A, mannan binding protein, wheat germ lectin, peanut lectin and avidchrom). Thus, the class of reactive antibody is distinguished.

In one embodiment of the disclosure, all of the reagents, including the colored labels, the reaction sites, and the site at which the sample is added, are all positioned in the same plane within the same test strip. In this embodiment of the disclosure, for example, the colored labels may be embedded or absorbed within the sorbent material of the test strip.

In another embodiment of the disclosure, at least one of the reagents, including the colored labels, the reaction sites, and the site at which the sample is added, are placed on a pad or site that resides on top of said test strip.

In another embodiment of the disclosure, the sample site is positioned between the labeling site and the first binding site.

In yet another embodiment of the disclosure, the sample being tested may be an antigen or analyte, or some other biological or chemical substance, and the immobilized

BRIEF DESCRIPTION OF THE DRAWINGS

The disclosure will be better understood and further objects, characterizing features, details and advantages thereof will appear more clearly as the following description proceeds with reference to the accompanying diagrammatic drawings given by way of non limiting example only illustrating a presently preferred specific embodiment of the disclosure.

FIG. 1 is a perspective view of one embodiment of the lateral flow immunoassay test;

FIG. 2 is a perspective view of another embodiment of the lateral flow immunoassay test;

FIG. 3 is an exploded view of the lateral flow immunoassay test;

FIG. 4 is a side view of the test strip;

FIG. 5 is a view of the colored particles attached to the antigen;

FIG. 6 is an exploded view of another version of the lateral flow immunoassay test;

FIG. 7 is a side view of yet another version of the lateral flow test strip;

FIG. 8 is a schematic of the reactions taking place in another embodiment of the disclosure;

FIG. 9 is a perspective view of an embodiment of the lateral flow test strip;

FIG. 10 is a perspective view of another embodiment of the lateral flow test strip;

FIG. 11 is a perspective view of an another alternative embodiment of the invention;

FIG. 12 is a cross sectional side view of the alternative embodiment of the invention of FIG. 12 and FIG. 13 is cross sectional side view of yet another embodiment of the invention;

FIG. 14 is an overhead view of another embodiment of the invention; and

FIG. 15 is a frontal view of another embodiment of the invention.

DETAILED DESCRIPTION OF THE DISCLOSURE

The immunoassay lateral flow test system 1 comprises a casing 2, preferably plastic, surrounding a test strip 7. On the top surface of the test strip there is a sample opening 8 and an opening 30 for a chase release buffer (explained supra and infra). A test results opening 9 to show the results of the assay. The casing can take a number of different forms. In FIGS. 3 and 6, the casing has a top section 4 or 100, and a bottom section 5 or 101.

Within the top section 4 there is at least one channel 6 into which is fitted a test strip 7. The test strip 7 preferably has a membrane support 10. The membrane support 10 may be comprised of plastic, cardboard, or any other rigid material. On top of the membrane support 10 is a testing layer 11, preferably made out of nitrocellulose. On top of the nitrocellulose or testing layer 11 are the areas to which the appropriate reagents or antigens are applied or affixed. The nitrocellulose/testing layer may be affixed to the membrane support 10.

As shown in FIG. 4, in one embodiment of the invention at one section of the test strip 7 is the sample site 16 to which the sample is to be applied. This sample site 16 preferably has a sample pad 31 residing on top of the testing layer 11, to which the sample is transferred. The sample is preferably a bodily fluid. This fluid may be serum whole blood, plasma, colostrum, milk, saliva, tears, or urine sample from a human or other animal species.

Downstream from the sample site 16 or sample pad 31 is the antigen, for which the serum is being tested. Upstream from the sample site 16 is the site for the labeled analyte 12, which may reside on pad 13. The chase release buffer is added upstream from the labeled analyte after the sample has reached control line 22.

In a preferred embodiment of the invention (FIG. 5) for the testing of allergens, the labeled analytes are anti-IgE antibodies 15 which have been attached to gold particles 14. The gold particles 14 attached to the antibody 15 (or antigens in some instances, depending on the use of this lateral flow device) are preferably larger than 20 nm, more preferably in the range of about 20 to 100 nm, and most preferably in the range of 20 to 40 nm. The gold sol labeled antigens/antibodies 35 are dried and deposited on the strip 7.

The metal sol particles to be used in accordance with the present disclosure may be prepared by coupling the analyte directly to the gold particle. Additionally, the labeled component may be prepared by coupling the analyte to the particle using a biotin/avidin linkage. In this latter regard, the substance may be biotinylated and the metal containing particle coated with an avidin compound. The biotin on the analyte may then be reacted with the avidin compound on the particle to couple the substance and the particle together. In another alternative form of the disclosure, the labeled component may be prepared by coupling the analyte to a carrier such as bovine serum albumin (BSA), key hole lymphocyananin (KLH), or ovalbumin and using this to bind to the metal particles.

The metal sol particles to be used in accordance with the present disclosure may be prepared by methodologies which are well known. For instance, the preparation of gold sol particles is disclosed in an article by G. Frens, Nature, 241, 20-22 (1973). Additionally, the metal sol particles may be metal or metal compounds or polymer nuclei coated with metals or metal compounds, as described in U.S. Pat. No. 4,313,734. Other methods well known in the art may be used to attach the analyte to gold particles. The methods include but are not limited to covalent coupling and hydrophobic bonding. The metal sol particles may be made of platinum, gold, silver, selenium, or copper or any number of metal compounds which exhibit characteristic colors.

Similarly, the analyte does not necessarily have to be attached to a metal sol particle, but may instead be attached to dyed or fluorescent labeled microparticles such as latex, polystyrene, dextran, silica, polycarbonate, methylmethacrylates and carbon. The metal sol particles, dyed or fluorescent labeled microparticles should be visible to the naked eye or able to be read with an appropriate instrument (spectrophotometer, fluorescent reader, etc.).

There are a number of ways in which the gold labeled antigens 16 may be deposited on the strip 7.

In yet another embodiment of the disclosure, the analytes may be attached to microspheres. This has the effect of increasing the number of reactive sites (epitopes) in a given area. Analytes may be attached to these alternate solid phases by various methodologies.

For instance, reactive microspheres (MX-Covaspheres-.sup.R of diameter 0.5 micrometers or 0.9 micrometers) purchased from Duke Scientific Corporation, Pal Alto, Calif. 94303, or other suppliers, may be used to covalently attach analytes. The binding is at the amino groups of the protein if covalent methodology is used. In addition, hydrophobic or electrostatic domains in the protein may be used for passive coating. A suspension of the spheres is mixed after sonication with the antigens/antibodies in water or in a phosphate buffer solution, after which they are incubated at room temperature for 10-75 minutes. The mixture is then centrifuged and the pellets containing the antigen/antibody-linked microspheres are suspended in a buffer containing 1-5% wt/volume bovine serum albumin (BSA) for 1 hour at room temperature. The BSA blocks any unreacted surfaces of the microspheres. After one more centrifugation, the spheres are resuspended in buffer (TBS with 5% BSA) and stored at 4 degrees C. before using.

The solid phase particles may comprise any one of known, water dispersable particles, such as, the polystyrene latex particles disclosed in U.S. Pat. No. 3,088,875. Such solid phase materials simply consist of suspensions of small, water-insoluble particles to which antigens/antibodies are able to bind. Suitable solid phase particles are also disclosed, for example, in U.S. Pat. Nos. 4,184,849; 4,486,530; and 4,636,479.

In another embodiment of the disclosure, the analytes may be attached to fluorescent microspheres or fluorescent microparticles. Said fluorescent microparticles may be purchased from Duke Scientific, Palo Alta, Calif. 94303 and are listed as Green, Red, or Blue fluorescent 0.4 micron microspheres (Product Bulletin 93). They are also available from Molecular Probes, Eugene, Oreg. 97402 and are listed as FluoroSpheres; Blue, Yellow-Green, Nile Red, Orange, Red, Crimson, Dark Red and Far Red in micron sizes from 0.03 to 5.0. Other manufactures also supply fluorescent microspheres. Characteristically, fluorescent microspheres incorporate fluorescent dyes in the solid outer matrix or in the internal volume of the microsphere. The fluorescent spheres are typically detected by a fluorescent reader that excites molecules at one wavelength and detects the emission of fluorescent waves at another wavelength. For example, Molecular Probes Nile Red particles excite at 526 nm at emit at 574 nm, the Far Red excites at 680 nm and emits at 720 nm and the Blue excites at 365 nm and emits at 430 nm. In a lateral flow format, detection of fluorescent microparticles requires the use of a reflectance reader with an appropriate excitation source (HeNe, Argon, tungsten or diode laser) and an appropriate emission filter for detection. Use of diode lasers allows for use of detection systems that use low cost lasers with detection above 600 nm. Most background fluorescence is from molecules that emit fluorescence below 550 nm.

Fluorescent microspheres contain surface functional groups such as carboxylate, sulfate and aldehyde groups, making them suitable for covalent coupling of proteins and other amine containing biomolecules. In addition, sulfate, carboxyl and amidine microspheres are hydrophobic particles that will passively absorb almost any protein or lectin. Coating is thus similar as for non fluorescent microspheres (MX-Covaspheres or other latex microparticles). A suspension of the fluorescent spheres is mixed after sonication with the antigens/antibody in water or in a phosphate buffered solution, after which they are incubated at room temperature for 10-75 minutes. EDAC (soluble carbodiimide), succinimidyl esters and isothiocyanates as well as other crosslinking agents may be used for covalent coupling of proteins and lectins to the microspheres. After the protein has attached to the surface of the microparticles, the mixture is centrifuged and the pellets containing the antigen or antibody linked to the fluorescent microparticles are suspended in a buffer containing 1-5% bovine serum albumin for one hour. After one more centrifugation, the spheres are resuspended in buffer (TBS with 5% BSA or other appropriate buffers) and stored at 4 degrees C. before use.

The solid phase particles useful in connection with the disclosure may comprise, for example, particles of latex or of other support materials such as silica, agarose, glass, polyacrylamides, polymethyl methacrylates, carboxylate modified latex and Sepharose. Preferably, the particles will vary in size from about 0.2 microns to about 10 microns. In particular, useful commercially available materials include 0.99 micron carboxylate modified latex, cyanogen bromide activated Sepharose beads (Sigma), fused silica particles (Ciba Coming, lot #6), isothiocyanate glass (Sigma), Reactogel 25DF (Pierce) and Polybead—carboxylate monodisperse microspheres. In accordance with the disclosure, such particles may be coated with a layer of antigens coupled thereto in a manner known per se in the art to present the solid phase component.

The invention thus operates as follows:

In one embodiment of the invention there are four binding sites positioned at the site of the immobilized testing site. The first binding site 18 is preferably to bind IgM. The second binding site 19 is preferably a site to bind IgA. The third binding site 20 is for the binding of IgG and the fourth binding site 22 is for a control. More specifically, each binding site is in the form of a striped line along the width of the test strip opening 9. At the site of each binding site, there are anti-Ig immunoglobulins. For example, class specific antibodies are laid down on the test strip. For example, a goat anti-human IgM antibody is laid down at the first binding site 18, goat anti-human IgA antibody is laid down at the second site 19 and goat anti-human IgG antibody is laid down at the third binding site 20. At the control site there is immobilized a protein or substance containing sulfur residues that readily react with any colloidal gold compound. It can also be an antibody reactive with the proteins coated on the gold or microparticles surface. The antibodies reactive with IgM, IgA and IgG can be from affinity purification of immune sera from goats, rabbits, donkeys, sheep, chickens or other animals. It may also be monoclonal antibodies directed against IgM, IgA and IgG. The antibodies used are specific for the heavy chain portion of the IgM, IgA and IgG antibodies. Substances reactive with IgG (protein A, protein G, lentil lectin, jacalin, concanavilin A, mannan binding protein, wheat germ lectin, peanut lectin and avidchrom) may be substituted for the antibody to IgG or combined with said antibody.

In one embodiment, after the sample has been placed at the sample opening 8, the sample migrates to the immobilized testing site, where any appropriate reactions take place where the antibodies are reactive with the site, thus forming a first complex. A chase release buffer is then added upstream from, or at the site, of the labeled analytes. The labeled analytes are released and migrate to the site of the immobilized first complex(es), where the labeled analytes bind to the first complexes. When the labeled analytes (preferably gold labeled analytes) react with the first complex, a visible line emerges. The gold sol complex. Migration continues and complexes are captured on the control line of the test strip 7. Excess fluid is wicked into the absorbent pad 17.

In another use and embodiment of the invention, it is disclosed here and shown in FIGS. 8 and 9 that immobilized antigens 201 of the binding site 212 first be exposed to the antibodies 203 of the sample site 207. The antibodies 203 (if present) of the sample react or bind to the immobilized antigens 201 to form a first complex 204. Then, a chase release buffer is added to or upstream from the labeled analytes 206, positioned upstream from the sample site 207 of the lateral flow assay 208. The released labeled analytes 210 then migrate to the site 212 of the immobilized antigens 201, wherein the labeled analytes bind to the first complex 204, thereby forming a second complex 220 visible to the naked eye. The labeled analyte 210 is preferably a gold labeled anti-IgE antibody.

In another embodiment of the invention as shown in FIGS. 7 and 8, the labeled analytes 210 are incorporated, or, to describe the invention more succinctly, are absorbed into the actual test strip 100 at site 106. Similarly, the binding site 104 can be incorporated into the test strip 100, and the sample pad can similarly be eliminated, with direct application of the sample on to the test strip downstream 105 from said labeled analytes.

There are a number of advantages to first exposing the sample (to be tested) to the immobilized antigens to form a first complex before exposing the sample to the colorant. By allowing the "uninhibited" antibodies to bind to the antigens, there is less steric hindrance. The unlabeled antibody molecules of the sample have a steriochemistry which allows for easier binding between the samples antibodies and the appropriate antigens. Put another way, the unlabeled antibodies have less physical or sterical interference and tertiary modifications, thereby allowing a more antibodies to bind to the antigens. The labeled analyte does not mask any of the binding sites between the antigen and the antigen specific antibodies, thus making it easier to read positive test results.

As an alternative to a colorant, a fluorescent, radioactive, enzymatic, ruminant or any other kind of marker can be used as a label that can be read/detected by the naked eye or by the appropriate equipment known in the field.

As shown in FIG. 10, it should be noted that while antigens may be immobilized on the lateral flow assay at the test site of the strip 305, antibodies or other specific bind agents may be laid down at the test site 300 in those cases wherein the material to be tested is placed downstream from the labeled analyte 301. In other words, the method (of forming a first complex between the sample and the test site "reagents") may be used whether one is testing for different antibodies in the blood to various antigens, or testing for any other biological or chemical material. Hence, depending on the nature of the test being performed, a first complex may be formed between the sample and an antigen at the site of testing zone, the sample and an antibody at the site of the testing zone, or between the sample and any other material that will selectively bind to the sample being tested, with the sample placed between the labeling site and the immobilized testing site. As with the alternative embodiment of the present invention, the labeling site 301 may be comprised of an absorbent pad 302. Similarly, the sample site 303 may have a pad 304.

The outer plastic casing 400 (FIG. 11) has an opening 401 for the addition of the chase release agent, and an opening 402 for the addition of the sample to be tested downstream from 401 (and downstream from the immobilized analyte on the test strip) There is of course an opening 403 to read the test results.

There are other embodiments for that may also be considered for the proposed lateral flow device.

In one instance, as shown in FIGS. 12 and 13, a sample is added in a lateral flow device 500 through opening 501. The sample (assuming positive results) will first bind to the immobilized antigens present on the strip, thereby forming a first complex. After waiting a short time, the chase release buffer is added through the same opening 501 as that of the sample. The volume of the sample added is preferably more than the amount of the chase release buffer; hence, in a preferable use of the invention, only the chase release buffer causes the gold reagent 603 to migrate to the site of the testing zone 602 on the test strip 600, whereupon a second complex is formed, this time between the colorant reagent (gold reagent) and the first complex. For example, if an sample is being tested for antibodies to specific allergen, a reaction will first form between the sample's IgE antibodies and the allergen on the test strip, followed by a reaction between the gold labeled anti-IgE antibodies and the IgE-antigen complex(es). This method can be used to test for other antibodies, H. pylori, or any other appropriate substance.

In another embodiment of the device shown in FIG. 14, there is no need to have colorant or gold reagent residing on the test strip or in the test device 700. The sample is added to the sample site 701 (which may or may not have a sample pad) on test strip 700. After waiting until the sample has migrated to the control line 503 and has bound to the appropriate immobilized parts of the testing zone forming any appropriate first complexes, a liquid gold reagent (or appropriate colorant) is added through the same opening 500 as that of the sample. The liquid gold reagent will migrate to the site of the first complexes to form a second complex between the gold label reagent and the first complex(es).

It should be noted that once the appropriate antibodies or analyte that is being tested binds to the immobilized reagents, it will not be possible for any stray gold labeled-reagent-analyte complexes to bind to the testing site, because all or virtually all of the immobilized binding sites on the strip will have been occupied by the sample. It should further be note that virtually all of the sample migrates to testing site when first applied to the test strip in this alternative embodiment.

In yet another embodiment of the invention shown in FIG. 15, chase release buffer can be added to the bottom section 801 of plastic casing. Specifically, after sample has been added through sample openings 804 and allowed to migrate to the control line 806 of the testing site 805, chase release buffer is added to the openings 807 of the bottom section thereby forming a reservoir, whereupon the top section 802 and the bottom section 801 of the plastic casing are pushed together so that the reactions and flow process can be completed. Alternatively, any reservoir containing chase release buffer can be used to dip the ends of the test strips to begin the flow of the colorant.

Once again, like the other processes, this device and process can be used to test for antibodies, antigens, allergens, H. pylori or any analyte or sample.

A kit for testing various biological substances may be formed for field use of the lateral flow device. The kit could comprise: a chase release buffer; at least one test strip (as described above), and a plastic casing holding said at least one test strip in place, said plastic casings having a sample opening in which to add the sample. Where appropriate the kit can comprise the liquid gold reagents as described above in the various embodiments.

The problem of separating reactivities of antibody classes lies in the 10 to 15 fold excess of IgG over IgA and IgM specific antibody reactivity with analyte reaction sites. If the IgG is allowed to react at the same time or rate as other classes of antibody, the IgG will mask most if not all the analyte epitopes, thereby decreasing or eliminating the activity of the IgM and IgA class antibodies to the analyte.

To solve this problem, an IgG reacting substance (which can be, among others, protein A, protein G, an antibody to IgG, lentil lectin, jacalin, concanavilin A, mannan binding protein, wheat germ lectin, peanut lectin and avidchrom) is added to the sample pad in order to complex the IgG such that the molecular weight of the complex is greater than 1 million. This large complex travels sufficiently slower than IgA, IgM, and IgE, thereby allowing these antibodies to react prior to the IgG. After reacting with the colored solid phase, the various reacted complexes are captured specifically at three sites by the antibodies to IgM, IgA, and IgG, or a substance reactive with IgG (protein A, protein G, lentil lectin, jacalin, concanavilin A, mannan binding protein, wheat germ lectin, peanut lectin and avidchrom).

Similarly, when said sample site and/or sample pad are downstream from said labeling site, said IgG reacting substance may be placed at the sample site and/or sample pad or downstream from said sample but before the test site.

For example, to determine whether a person has been exposed to *Helicobacter pylori*, or to determine if there has been successful treatment of the disease, a serum sample is tested to determine whether it contains antibodies to *H. pylori*. Assuming the use of gold labels, if lines appear at the binding sites for IgG and weakly for IgM, then there is only a chronic condition present. If however, lines appear at the binding sites for IgM and IgA, with or without IgG, then an active or recent colonizing infection is occurring. The detection of IgA when combined with a low serum pepsinogen level is associated with an increased risk of gastric cancer.

This test can detect the presence of class specific antibodies reactive with any bacteria, virus, fungus, irritant, or protein. Some, but not all of the analytes which can be detected using this method include *Streptococcus* Group A, *Streptococcus* Group B, *Mycobacterium, Mycobacterium tuberculosis*, Mycoplasma, Chlamydiae, Rickettsiae, Herpes virus, CMV, Hepatitis A, Hepatitis C, Hepatitis B, Influenza, HIV I, HIV II, HTLV I & II, Chagus, Toxoplasma, Helminh, Nematodes, autoimmune antigens, antibodies to heat shock proteins, transplantation analytes, histocompatability analytes, and combinations thereof.

In another embodiment of the disclosure, this lateral flow assay can be used for the visual detection of allergen specific IgE antibodies in human or animal bodily fluids. In this assay the test serum reacts with a calorimetric (preferably gold) labeled anti-IgE antibody contained in the calorimetric (preferably dried) gold pad 16. The resulting complex travels along the test strip to the line stripped allergen site 24. At the allergen site, there are a plurality of immobilized allergens 24. Indeed, the immunoassay can easily test for one or more different allergens, preferably by one strip 25, two strips (25 and 26) or multiple strips next to each other. Each strip can contain one or more specific allergen lines. The common allergens which may be tested include but are not limited to pollens (Timothy, cultivated rye, birch, alder, hazelnut, mugwort, English plantain, ragweed, nettle, etc.), dust allergens (*D. farinae, D. pteronyssinus*, house dust), molds (*Alternaria tenuis, Aspergillus fum., Cladosporium, Penicillium not*), animal epithelium (Cat epithelium, dog dander, horse dander, goose feathers) foods (dairy, cereals, nuts, seafoods, legumes and mixes thereof), inhalant mixes (pollen I (grasses), pollen II (weed/trees), animal mix, dust mix, mold mix) and combinations thereof. The allergens are immobilized on the test strip by the use of solubilizing agents such as sugars and alcohols (sucrose, mannose, fructose, ethylene glycol, ethanol, methanol, glycerin, dextrans). The use of sugars and alcohols unfolds the allergen protein tertiary structure such that more hydrophobic domains are exposed allowing greater binding to the membrane. In addition, protein to protein aggregation is reduced through solubilization allowing individual protein molecules to bind to the nitrocellulose or nylon membrane.

It should be noted that, in addition to the use of sugars and alcohols, the protein molecules or reagents may be immobilized on the test strip by the use of other materials, including but not limited to fats, gels, simple buffers, specially designed molecules.

Assuming there is a reaction between the complexes of gold labeled anti IgE antibody and the sample containing IgE antibody and the allergens, a red line will appear at the site of the allergen when there is a positive response. The assay validity is demonstrated by the appearance of a red colored line in the positive control region of the membrane. The positive control is a protein or substance containing sulfur residues that readily react with any colloidal gold compound. It can also be an antibody reactive with the proteins coated on the gold or in the sample. Since the gold or microparticles conjugate is in excess, sufficient conjugate is available to react with the control line.

Many modifications and variations of the present disclosure are possible in light of the above teachings. It is, therefore, to be understood within the scope of the appended claims the disclosure may be protected otherwise than as specifically described.

What is claimed is:

1. A method of detecting immune reactants, comprising:
    a) placing a sample containing antibodies on a lateral flow immunoassay device, said device comprising:
        at least one test strip, said at least one test strip comprising:
            i) a sample site for applying a sample comprising antibodies;
            ii) a plurality of reaction sites downstream from said sample site, each said reaction site containing a different allergen such that when IgE antibodies come in contact with an antigen to which the IgE antibodies react, a first complex is formed;
            iii) a colorimetric labeled analyte site comprising dried colorimetric labeled anti-IgE antibodies, said colorimetric labeled analyte site positioned upstream from said sample site; and
            iv) a location on said test strip to add a chase release buffer for the release of said colored labeled analyte, after the addition of the liquid sample to said sample site, said location for adding said chase release buffer being located at the site of or upstream from said colorimetric labeled analyte site;
    b) allowing said test sample to migrate from the sample site to the reaction sites wherein said anti-IgE antibodies and said allergens combine to form said first complex comprising an anti-IgE antibody-allergen complex;
    c) adding said chase release buffer at or above the site of the colorimetric labeled analyte site;
    d) allowing time for said chase release buffer and said colorimetric labeled analyte to flow downstream to the side of said reaction sites; and
    e) reading said lateral flow immunoassay device, wherein a colored line, indicating a positive response develops when said colorimetric labeled anti-IgE antibodies come in contact with said first complex, thereby forming a second complex comprising a colorimetric labeled anti-IgE antibody-IgE antibody-allergen complex.

2. The method of claim 1, wherein said allergens are selected from the group consisting of pollens, dust mite allergens, molds, animal epithelium, foods, allergen mixes, and combinations thereof.

3. The method of claim 1, wherein said immunoassay comprises at least two test strips.

4. The method of claim 1, further comprising at least one solubilizing agent to immobilize any said allergen, said at least one solubilizing agent being present in an amount such that said allergen protein tertiary structure unfolds to allow for greater binding of said antigen to said test strip, wherein, said solubilizing agent is selected from the group consisting of sugars and alcohol.

5. The method of claim 4, wherein at least one solubilizing agent is selected from the group consisting of sucrose, mannose, fructose, ethylene glycol, ethanol, methanol, glycerin and dextrans.

6. The method of claim 5, wherein said sugar is selected from the group consisting of sucrose, mannose, fructose, dextran, and combinations thereof.

7. The method of claim 4, wherein said wherein said alcohol is selected from the group consisting of ethylene glycol, glycerol, ethanol, methanol, and combinations thereof.

* * * * *

UNITED STATES PATENT AND TRADEMARK OFFICE
CERTIFICATE OF CORRECTION

PATENT NO. : 7,629,127 B2
APPLICATION NO. : 11/038076
DATED : December 8, 2009
INVENTOR(S) : Thomas T. Hubscher It is certified that error appears in the above-identified patent and that said Letters Patent is hereby corrected as shown below:

Column 12, line 19-57, Please amendment claim 1 as follows:

1. A method of detecting immune reactants, comprising:

a) placing a sample containing antibodies on a lateral flow immunoassay device, said device comprising[:] at least one test strip, said at least one test strip comprising:

i) a sample site for applying a sample comprising antibodies;

ii) a plurality of reaction sites downstream from said sample site, each said reaction site containing a different allergen such that when IgE antibodies come in contact with an antigen to which the IgE antibodies react, a first complex is formed;

iii) a colorimetric labeled analyte site comprising dried colorimetric labeled anti-IgE antibodies, said colorimetric labeled analyte site positioned upstream from said sample site; and iv) a location on said test strip to add a chase release buffer for the release of said colored labeled analyte, after the addition of the liquid sample to said sample site, said location for adding said chase release buffer being located at the site of or upstream from said colorimetric labeled analyte site;

b) allowing said test sample to migrate from the sample site to the reaction sites wherein said [anti-IgE] IgE antibodies and said allergens combine to form said first complex comprising an [anti-IgE] IgE antibody-allergen complex;

c) adding said chase release buffer at or above the site of the colorimetric labeled analyte site;

d) allowing time for said chase release buffer and said colorimetric labeled analyte to flow downstream to the side of said reaction sites; and e) reading said lateral flow immunoassay device, wherein a colored line, indicating a positive response develops when said colorimetric labeled anti-IgE antibodies come in contact with said first complex, thereby forming a second complex comprising a colorimetric labeled anti-IgE antibody-IgE Signed and Sealed this
Nineteenth Day of February, 2013

Teresa Stanek Rea
*Acting Director of the United States Patent and Trademark Office* antibody-allergen complex.